US005679582A

United States Patent [19]

Bowie et al.

[11] Patent Number: 5,679,582
[45] Date of Patent: *Oct. 21, 1997

[54] SCREENING METHOD FOR IDENTIFYING LIGANDS FOR TARGET PROTEINS

[75] Inventors: James U. Bowie, Culver City, Calif.; Andrew Pakula, Lexington, Mass.

[73] Assignee: Scriptgen Pharmaceuticals, Inc., Medford, Mass.

[*] Notice: The term of this patent shall not extend beyond the expiration date of Pat. No. 5,585,277.

[21] Appl. No.: 263,923

[22] Filed: Jun. 21, 1994

Related U.S. Application Data

[63] Continuation-in-part of Ser. No. 80,829, Jun. 21, 1993, abandoned.

[51] Int. Cl.⁶ ..................................................... G01N 33/53
[52] U.S. Cl. .......................... 436/518; 436/501; 435/23; 435/24; 435/4; 435/7.92
[58] Field of Search ................................. 435/23, 24, 4, 435/7.92, 7.9; 436/501, 518

[56] References Cited

U.S. PATENT DOCUMENTS

| | | | |
|---|---|---|---|
| 4,859,609 | 8/1989 | Dull et al. | 436/501 |
| 5,506,097 | 4/1996 | Potter et al. | 435/4 |
| 5,585,277 | 12/1996 | Bowie et al. | 436/518 |

FOREIGN PATENT DOCUMENTS

| | | |
|---|---|---|
| 0 613 007 A2 | 8/1994 | European Pat. Off. . |
| WO 92/03542 | 3/1992 | WIPO . |
| WO 93/14781 | 8/1993 | WIPO . |

OTHER PUBLICATIONS

Derwent Publications, Abstract No. 75-43214W, Japanese Patent No. A-49 093 093, Sep. 4, 1974.

Tanigaki, N., et al, *Human Immunology*, vol. 36, pp. 119-127, 1993.

Grant, S.K., et al, *Biochemistry*, vol. 31, pp. 9491-9501, 1992.

Randall, L.L., *Science*, vol. 257, pp. 241-245, Jul. 1992.

*Primary Examiner*—Toni R. Scheiner
*Attorney, Agent, or Firm*—Darby & Darby

[57] ABSTRACT

A novel method for screening chemical compounds, test ligands, for potential pharmaceutical effectiveness. The disclosed method identifies possible therapeutic test ligands by placing them in the presence of target proteins and determining the ability of test ligands to increase the ratio of folded target protein to unfolded target protein. This differs significantly from known methods of novel pharmaceutical testing in that the biochemical function of the target protein need not be known and, except for one of the five embodiments of the method, the existence of any known ligands of the target protein is unnecessary.

47 Claims, 7 Drawing Sheets

SCREENING METHOD FOR IDENTIFYING LIGANDS FOR TARGET PROTEINS

This application is a Continuation-in-Part of U.S. application Ser. No. 08/080,829, filed Jun. 21, 1993, now abandoned.

FIELD OF THE INVENTION

This invention pertains to novel methods for high-throughput screening for pharmaceutical compounds, in particular those that bind to proteins involved in pathogenesis of disease or in regulation of a physiological function.

BACKGROUND OF THE INVENTION

Pharmaceuticals can be developed from lead compounds that are identified through a random screening process directed towards a target, such as a receptor. Large scale screening approaches can be complicated by a number of factors. First, many assays are laborious or expensive to perform. Assays may involve experimental animals, cell lines, or tissue cultures that are difficult or expensive to acquire or maintain. They may require the use of radioactive materials, and thus pose safety and disposal problems. These considerations often place practical limitations on the number of compounds that reasonably can be screened. Thus, those employing random screening methods are frequently forced to limit their search to those compounds for which some prior knowledge suggests that the compounds are likely to be effective. This strategy limits the range of compounds tested, and many useful drugs may be overlooked.

Furthermore, the specificity of many biochemical assays may exclude a wide variety of useful chemical compounds, because the interactions between the ligand and the receptor protein are outside the scope of the assay. For example, many proteins have multiple functions, whereas most assays are capable of monitoring only one such activity. With such a specific assay, many potential pharmaceuticals may not be detected.

Finally, in most existing biochemical screening approaches to drug discovery, the activity of the target protein must be defined. This requires that the system in question be well-characterized before screening can begin. Even when a protein sequence is known, as in e.g. a newly cloned gene, the specific functions of the protein may not be revealed simply by analysis of its sequence. Consequently, biochemical screening for therapeutic drugs directed against many target proteins must await detailed biochemical characterization, a process that generally requires extensive research.

Thus, there is a need in the art for a rapid, cost-effective, high-throughput assay that enables the screening of large numbers of compounds for their ability to bind therapeutically or physiologically relevant proteins. Furthermore, there is a need in the art for screening methods that are independent of the biological activity of the target proteins, and that will detect compounds that bind regions of the target proteins other than biologically active domains.

SUMMARY OF THE INVENTION

The present invention provides a method for identifying a ligand that binds a target protein. According to the method, the target protein is incubated in the presence of a test ligand to produce a test combination, and in the absence of a test ligand to produce a control combination. The test and control combinations are then treated to cause a detectable fraction of the target protein to exist in a partially or totally unfolded state. The extent to which the target protein occurs in a folded state, an unfolded state, or both, in the test and control combinations is then determined. When the target protein is present in the folded state to a greater or lesser extent in the test combination than in the control combination, the test ligand is a ligand that binds the target protein.

DETAILED DESCRIPTION OF THE INVENTION

Figure 1:
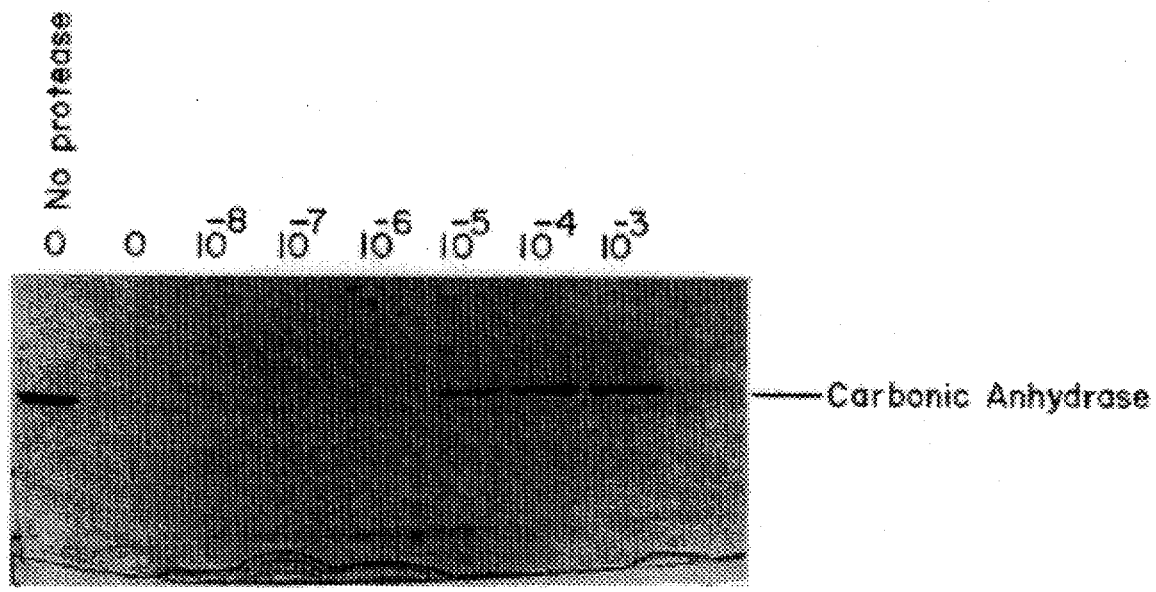
FIG. 1 shows an SDS-polyacrylamide gel profile of carbonic anhydrase after proteolysis in the absence and presence of increasing concentrations of acetazolamide.

All patent applications, patents, and literature references cited in this specification are hereby incorporated by reference in their entirety. In case of conflict, the present description, including definitions, will prevail.

Definitions

As used herein, the term "ligand" refers to an agent that binds a target protein. The agent may bind the target protein when the target protein is in its native conformation, or when it is partially or totally unfolded or denatured. According to the present invention, a ligand is not limited to an agent that binds a recognized functional region of the target protein e.g. the active site of an enzyme, the antigen-combining site of an antibody, the hormone-binding site of a receptor, a cofactor-binding site, and the like. In practicing the present invention, a ligand can also be an agent that binds any surface or internal sequences or conformational domains of the target protein. Therefore, the ligands of the present invention encompass agents that in and of themselves may have no apparent biological function, beyond their ability to bind to the target protein in the manner described above.

As used herein, the term "test ligand" refers to an agent, comprising a compound, molecule or complex, which is being tested for its ability to bind to a target protein. Test ligands can be virtually any agent, including without limitation metals, peptides, proteins, lipids, polysaccharides, nucleic acids, small organic molecules, and combination thereof. Complex mixtures of substances such as natural product extracts, which may include more than one test ligand, can also be tested, and the component that binds the target protein can be purified from the mixture in a subsequent step.

As used herein, the term "target protein" refers to a peptide, protein or protein complex for which identification of a ligand or binding partner is desired. Target proteins include without limitation peptides or proteins known or believed to be involved in the etiology of a given disease, condition or pathophysiological state, or in the regulation of physiological function. Target proteins may be derived from any living organism, such as a vertebrate, particularly a mammal and even more particularly a human. For use in the present invention, it is not necessary that the protein's biochemical function be specifically identified. Target proteins include without limitation receptors, enzymes, oncogene products, tumor suppressor gene products, vital proteins, and transcription factors, either in purified form or as part of a complex mixture of proteins and other compounds. Furthermore, target proteins may comprise wild type proteins, or, alternatively, mutant or variant proteins, including those with altered stability, activity, or other variant properties, or hybrid proteins to which foreign amino acid sequences e.g. sequences that facilitate purification have been added.

As used herein, "test combination" refers to the combination of a test ligand and a target protein. "Control combination" refers to the target protein in the absence of a test ligand.

As used herein, the "folded state" of a protein refers to the native or undenatured form of the protein as it is present in its natural environment, or after isolation or purification, i.e. before exposure to denaturing conditions. Similarly, the "unfolded state" refers to a situation in which the polypeptide has lost elements of its secondary and/or tertiary structure that are present in its "folded state." It will be recognized by those skilled in the art that it is difficult to determine experimentally when a polypeptide has become completly unfolded i.e. has lost all elements of secondary and tertiary structure. Thus, the term "unfolded state" as used herein encompasses partial or total unfolding.

As used herein, "detectable fraction" refers to a quantity that is empirically determined and that will vary depending upon the method used to distinguish folded from unfolded protein. For example, when protease sensitivity is used to monitor folding, conditions are chosen (e.g. by adjusting temperature or adding denaturants) so that approximately 80% of the target protein is digested within a convenient incubation period. Alternatively, when antibodies specific to the folded or unfolded state of a target protein are used as the detection method, conditions are chosen so that a sufficient amount of antibody is bound to give a detectable signal.

The present invention encompasses high-throughput screening methods for identifying a ligand that binds a target protein. If the target protein to which the test ligand binds is associated with or causative of a disease or condition, the ligand may be useful for diagnosing, preventing or treating the disease or condition. A ligand identified by the present method can also be one that is used in a purification or separation method, such as a method that results in purification or separation of the target protein from a mixture. The present invention also relates to ligands identified by the present method and their therapeutic uses (for diagnostic, preventive or treatment purposes) and uses in purification and separation methods.

According to the present invention, a ligand for a target protein is identified by its ability to influence the extent of folding or the rate of folding or unfolding of the target protein. Experimental conditions are chosen so that the target protein is subjected to unfolding, whether reversible or irreversible. If the test ligand binds to the target protein under these conditions, the relative amount of folded:unfolded target protein or the rate of folding or unfolding of the target protein in the presence of the test ligand will be different, i.e. higher or lower, than that observed in the absence of the test ligand. Thus, the present method encompasses incubating the target protein in the presence and absence of a test ligand, under conditions in which (in the absence of ligand) the target protein would partially or totally unfold. This is followed by analysis of the absolute or relative amounts of folded vs. unfolded target protein or of the rate of folding or unfolding of the target protein.

An important feature of the present invention is that it will detect any compound that binds to any sequence or domain of the target protein, not only to sequences or domains that are intimately involved in a biological activity or function. The binding sequence, region, or domain may be present on the surface of the target protein when it is in its folded state, or may be buried in the interior of the protein. Some binding sites may only become accessible to ligand binding when the protein is partially or totally unfolded.

In practicing the present invention, the test ligand is combined with a target protein, and the mixture is maintained under appropriate conditions and for a sufficient time to allow binding of the test ligand to the target protein. Experimental conditions are determined empirically for each target protein. When testing multiple test ligands, incubation conditions are chosen so that most ligand:target protein interactions would be expected to proceed to completion. In general, the test ligand is present in molar excess relative to the target protein. The target protein can be in a soluble form, or, alternatively, can be bound to a solid phase matrix. The matrix may comprise without limitation beads, membrane filters, plastic surfaces, or other suitable solid supports.

For each target protein, appropriate experimental conditions, e.g. temperature, time, pH, salt concentration, and additional components, are chosen so that a detectible fraction of the protein is present in an unfolded form in the absence of test ligand. For a target protein that unfolds irreversibly, preferred experimental conditions allow a detectable amount of the protein to unfold during a convenient incubation period in the absence of test ligand. To adjust or optimize the ratio of folded:unfolded protein or the rate of folding or unfolding, denaturing conditions may be required, including the use of elevated temperatures, the addition of chaotropes or denaturants such as urea or guanidinium or guanidium salts such as guanidinium thiocyanate, detergents, or combinations thereof. Furthermore, mutant proteins that contain stabilizing or destabilizing amino acid substitutions may be used to manipulate the folded:unfolded ratio.

The time necessary for binding of target protein to ligand will vary depending on the test ligand, target protein and other conditions used. In some cases, binding will occur instantaneously (e.g., essentially simultaneous with combination of test ligand and target protein), while in others, the test ligand-target protein combination is maintained for a longer time e.g. up to 12–16 hours, before binding is detected. When many test ligands are employed, an incubation time is chosen that is sufficient for most protein:ligand interactions. In the case of target proteins that unfold irreversibly, the rate of unfolding must also be taken into consideration in determining an appropriate time for binding of test ligand.

Binding of a test ligand to the target protein is assessed by comparing the absolute amount of folded or unfolded target protein in the absence and presence of test ligand, or, alternatively, by determining the ratio of folded:unfolded target protein or the rate of target protein folding or unfolding in the absence and presence of test ligand. If a test ligand binds the target protein (i.e., if the test ligand is a ligand for the target protein), there may be significantly more folded, and less unfolded, target protein (and, thus, a higher ratio of folded to unfolded target protein) than is present in the absence of a test ligand. Alternatively, binding of the test ligand may result in significantly less folded, and more unfolded, target protein than is present in the absence of a test ligand. Similarly, binding of the test ligand may cause the rate of target protein folding or unfolding to change significantly.

In either case, determination of the absolute amounts of folded and unfolded target protein, the folded:unfolded ratio, or the rates of folding or unfolding, may be carried out using one of the known methods as described below. These methods include without limitation proteolysis of the target protein, binding of the target protein to appropriate surfaces, binding of specific antibodies to the target protein, binding of the target protein to molecular chaperones, binding of the target protein to immobilized ligands, and measurement of aggregation of the target protein. Other physico-chemical techniques may also be used, either alone or in conjunction with the above methods; these include without limitation measurements of circular dichroism, ultraviolet and fluorescence spectroscopy, and calorimetry. A preferred embodiment involves measuring the relative proteolysis of a target protein following incubation in the absence and presence of a test ligand. However, it will be recognized by those skilled in the art that each target protein may have unique properties that make a particular detection method most suitable for the purposes of the present invention.

For the purposes of high-throughput screening, the experimental conditions described above are adjusted to achieve a threshold proportion of test ligands identified as "positive" compounds or ligands from among the total compounds screened. This threshold is set according to two criteria. First, the number of positive compounds should be manageable in practical terms. Second, the number of positive compounds should reflect ligands with an appreciable affinity towards the target protein. A preferred threshold is achieved when 0.1% to 1% of the total test ligands are shown to be ligands of a given target protein.

Binding to a given protein is a prerequisite for pharmaceuticals intended to modify directly the action of that protein. Thus, if a test ligand is shown, through use of the present method, to bind a protein that reflects or affects the etiology of a condition, it may indicate the potential ability of the test ligand to alter protein function and to be an effective pharmaceutical or lead compound for the development of such a pharmaceutical. Alternatively, the ligand may serve as the basis for the construction of hybrid compounds containing an additional component that has the potential to alter the protein's function. In this case, binding of the ligand to the target protein serves to anchor or orient the additional component so as to effectuate its pharmaceutical effects. For example, a known compound that inhibits the activity of a family of related enzymes may be rendered specific to one member of the family by conjugation of the known compound to a ligand, identified by the methods of the present invention, that binds specifically to that member at a different site than that recognized by the known compound.

The fact that the present method is based on physico-chemical properties common to most proteins gives it widespread application. The present invention can be applied to large-scale systematic high-throughput procedures that allow a cost-effective screening of many thousands of test ligands. Once a ligand has been identified by the methods of the present invention, it can be further analyzed in more detail using known methods specific to the particular target protein used. For example, the ligand can be tested for binding to the target protein directly e.g. by incubating radiolabelled ligand with unlabelled target protein, and then separating protein-bound and unbound ligand. Furthermore, the ligand can be tested for its ability to influence, either positively or negatively, a known biological activity of the target protein.

In a preferred embodiment of the present invention, binding of test ligand to target protein is detected through the use of proteolysis. This assay is based on the increased susceptibility of unfolded, denatured polypeptides to protease digestion relative to that of folded proteins. In this case, the test ligand-target protein combination, and a control combination lacking the test ligand, are treated with one or more proteases that act preferentially upon unfolded target protein. After an appropriate period of incubation, the level of intact i.e. unproteolysed target protein is assessed using one of the methods described below e.g. gel electrophoresis and/or immunoassay.

There are two possible outcomes that indicate that the test ligand has bound the target protein. Either a significantly higher, or significantly lower, absolute amount of intact or degraded protein may be observed in the presence of ligand than in its absence.

Proteases useful in practicing the present invention include without limitation trypsin, chymotrypsin, V8 protease, elastase, carboxypeptidase, proteinase K, thermolysin and subtilisin (all of which can be obtained from Sigma Chemical Co., St. Louis, Mo.). The most important criterion in selecting a protease or proteases for use in practicing the present invention is that the protease(s) must be capable of digesting the particular target protein under the chosen incubation conditions, and that this activity be preferentially directed towards the unfolded form of the protein. To avoid "false positive" results caused by test ligands that directly inhibit the protease, more than one protease, particularly proteases with different enzymatic mechanisms of action, can be used simultaneously or in parallel assays. In addition, cofactors that are required for the activity of the protease(s) are provided in excess, to avoid false positive results due to test ligands that may sequester these factors.

Typically, a purified target protein is first taken up to a final concentration of 2–100 µg/ml in a buffer containing 50 mM Tris-HCl, pH 7.5, 10 mM calcium acetate and 0.034 mg/ml bovine serum albumin. Proteinase K and thermolysin, proteases with distinct mechanisms of action, are then added to a final concentration of 2–10 µg/ml. Parallel incubations are then performed for different time periods ranging from 5 minutes to one hour, at temperatures ranging from 20° C. to 65° C. Reactions are terminated by addition of phenylmethylsulfonyl chloride (PMSF) to a final concentration of 1 mM and ethylenediaminotetraacetic acid (EDTA) to a final concentration of 20 mM. The amount of intact protein remaining in the reaction mixture at the end of the incubation period is then assessed by any of the following methods: polyacrylamide gel electrophoresis, ELISA, or binding to nitrocellulose filters.

The above protocol allows the selection of appropriate conditions that result in digestion of approximately 80% of the target protein, indicating that a significant degree of unfolding has occurred. If a known ligand for the target protein is available, the ligand is included in the reaction mixture at a concentration of 20–200 µM, and the experiment is repeated. Typically, at least a two-fold increase or decrease in the level of intact target protein is observed, indicating that binding of a known ligand changes the ratio of folded:unfolded target protein and/or the rate of folding or unfolding.

Once conditions are established for high-throughput screening as described above, the protocol is repeated simultaneously with a large number of test ligands at concentrations ranging from 20 to 200 µM. Observation of at least a two-fold increase or decrease in the level of intact protein signifies a "hit" compound i.e. a ligand that binds the target protein. Preferred conditions are those in which between 0.1 and 1% of test ligands are identified as "hit" compounds using this procedure.

In another embodiment, the relative amount of folded and unfolded target protein in the presence and absence of test ligand is assessed by measuring the relative amount of target protein that binds to an appropriate surface. This method takes advantage of the increased propensity of unfolded proteins to adhere to surfaces, which is due to the increased surface area, and decrease in masking of hydrophobic residues, that results from unfolding. If a test ligand binds a target protein (i.e., is a ligand of the target protein), it may stabilize the folded form of the target protein and decrease its binding to a solid surface. Alternatively, a ligand may stabilize the unfolded form of the protein and increase its binding to a solid surface.

In this embodiment, the target protein, a test ligand and a surface that preferentially binds unfolded protein are combined and maintained under conditions appropriate for binding of the target protein to a ligand and binding of unfolded target protein to the surface. Alternatively, the target protein and test ligand can be pre-incubated in the absence of the surface to allow binding. Surfaces suitable for this purpose include without limitation microliter plates constructed from a variety of treated or untreated plastics, plates treated for tissue culture or for high protein binding, nitrocellulose filters and PVDF filters.

Determination of the amount of surface-bound target protein or the amount of target protein remaining in solution can be carried out using standard methods known in the art e.g. determination of radioactivity or immunoassay. If significantly more or less target protein is surface bound in the presence of a test ligand than in the absence of the test ligand, the test ligand is a ligand of the target protein. Similarly, the ratio of surface-bound:soluble target protein will be significantly greater or smaller in the presence of a test ligand than in its absence, if a test ligand is a ligand for the target protein.

In another embodiment, the extent to which folded and unfolded target protein are present in the test combination is assessed through the use of antibodies specific for either the unfolded state or the folded state of the protein i.e. denatured-specific ("DS"), or nature-specific ("NS") antibodies, respectively. (Breyer, 1989, *J. Biol. Chem.,* 264 (5):13348–13354).

Polyclonal and monoclonal DS and NS antibodies specific for particular target proteins can be prepared by methods that are well known in the art (E. Harlow & D. Lane, ANTIBODIES: A LABORATORY MANUAL, Cold Spring Harbor Laboratory, 1988; Zola, Monoclonal Antibodies: A Manual of Techniques, CRC Press, Inc., Boca Raton, Fla., 1987). For DS antibodies, animals can be immunized with a peptide from a region of the protein that is buried in the interior of the protein when it is in the native state. If the three-dimensional structure of the protein is unknown, antibodies are prepared against several peptides and then screened for preferential binding to the denatured state. For NS antibodies, intact non-denatured protein is used as an immunogen, and the resulting antibodies are screened for preferential binding to the native protein and purified for use in the present invention.

DS or NS antibodies can be utilized to detect a ligand-induced change in the level of folded target protein, unfolded target protein, the folded:unfolded ratio, or the rate of folding or unfolding.

In one approach, a test combination containing the DS antibody, the target protein, and the test ligand is exposed to a solid support e.g. a microtiter plate coated with the denatured target protein or a peptide fragment thereof, under conditions appropriate for binding of the target protein with its ligand and binding of the DS antibody to unfolded target protein. A control combination, which is the same as the test combination except that it does not contain test ligand, is processed in the same manner as the test solution. By comparing the amount of antibody bound to the plate or the amount remaining in solution in the test and control combinations, the difference in target protein folding is detected. The amount of antibody bound to the plate or remaining in solution can be measured as described below.

In a second approach, a test combination containing the DS antibody, the test ligand, and the target protein is exposed to a solid support coated with a second antibody, referred to as a solid phase antibody, which cannot bind to the target protein simultaneously with the DS antibody, and is specific for the target protein, but is either specific for the folded state (NS antibody) or unable to differentiate between the native and denatured states ("non-differentiating" or "ND" antibody). The resulting test combination or solution is maintained under conditions appropriate for binding of the target protein with a ligand of the target protein and for binding of the antibodies to the proteins they recognize. A control combination, which is the same as the test solution except that it does not contain test ligand, is processed in the same manner as the test solution. In both combinations, denatured (unfolded) target protein binds the DS antibody and is inhibited from binding the solid phase antibody. The ability of the test ligand to bind the target protein can be gauged by determining the amount of target protein that binds to the solid phase antibody in the test solution and comparing it with the extent to which target protein binds to the solid phase antibody in the absence of test ligand, which in turn reflects the amount of target protein in the folded state. The amount of target protein bound to the plate via the second antibody or remaining in solution can be detected by the methods described below. This approach may be used in a comparable manner with NS antibody as the soluble antibody and DS or ND antibody on the solid phase.

In a third approach, a test solution containing the target protein and the test ligand is exposed to a solid support e.g. a microtiter plate that has been coated with a DS or NS antibody and maintained under conditions appropriate for binding of target protein to its ligand and for binding of the antibody to target protein. Alternatively, the antibody can be present on the surfaces of beads. The ability of the test ligand to bind the target protein is gauged by determining the extent to which target protein remains in solution (unbound to the antibody) or on the solid surface (bound to the antibody), or the ratio of the two, in the presence and in the absence of test ligand. Alternatively, the antibody can be present in solution and the target protein can be attached to a solid phase, such as a plate surface or bead surface.

In another embodiment, molecular chaperones are used to assess the relative levels of folded and unfolded protein in a test combination. Chaperones encompass known proteins that bind unfolded proteins as part of their normal physiological function. They are generally involved in assembling oligomeric proteins, in ensuring that certain proteins fold correctly, in facilitating protein localization, and in preventing the formation of proteinaceous aggregates during physiological stress (Hardy, 1991, *Science*, 251:439–443). These proteins have the ability to interact with many unfolded or partially denatured proteins without specific recognition of defined sequence motifs.

One molecular chaperone, found in *E. coli*, is a protein known as SecB. SecB has a demonstrated involvement in export of a subset of otherwise unrelated proteins. Competition experiments have shown that SecB binds tightly to all the unfolded proteins tested, including proteins outside of its particular export subset, but does not appear to interact with the folded protein. Other chaperones suitable for use in the present invention include without limitation heat shock protein 70s, heat shock protein 90s, GroEI and GroES (Gething et al., *Nature* 355:33, 1992).

In this embodiment, a test combination containing the test ligand and the target is exposed to a solid support e.g. microliter plate or other suitable surface coated with a molecular chaperone, under conditions appropriate for binding of target protein with its ligand and binding of the molecular chaperone to unfolded target protein. The unfolded target protein in the solution will have a greater tendency to bind to the molecular chaperone-covered surface relative to the ligand-stabilized folded target protein. Thus, the ability of the test ligand to bind target protein can be determined by determining the amount of target protein remaining unbound, or the amount bound to the chaperone-coated surface.

Alternatively, a competition assay for binding to molecular chaperones can be utilized. A test combination containing purified target protein, the test ligand, and a molecular chaperone can be exposed to a solid support e.g. a microtiter well coated with denatured (unfolded) target protein, under conditions appropriate for binding target protein with its ligand and binding of the molecular chaperone to unfolded target protein. A control combination, which is the same as the test combination except that it does not contain test ligand, is processed in the same manner. Denatured target protein in solution will bind to the chaperone and thus inhibit its binding to the denatured target protein bound to the support. Binding of a test ligand to the target protein will result in a difference in the amount of unfolded target protein, and, thus, more or less chaperone will be available to bind to the solid-phase denatured target protein than is the case in the absence of binding of test ligand. Thus, binding of test ligand can be determined by assessing chaperone bound to the surface or in solution in the test combination and in the control combination and comparing the results. In this assay, the chaperones are generally not provided in excess, so that competition for their binding can be measured.

Alternatively, a test combination containing the target protein, the test ligand and a molecular chaperone can be exposed to a solid support e.g. a microtiter well that has been coated with antisera or a monoclonal antibody specific for the folded target protein (NS antibody) and unable to bind the target protein bound to the chaperone. Unfolded target protein will bind chaperone in solution and thus be inhibited from binding the solid phase antibody. By detecting target protein in the solution or bound to the well walls and comparing the extent of either or both in an appropriate control (the same combination without the test ligand), the ability of the test ligand to bind target protein can be determined. If the test ligand is a ligand for the target protein, more or less target protein will be bound to the antisera or monoclonal antibody bound to the container surface in the test combination than in the control combination, and correspondingly more or less target protein will be present unbound (in solution) in the test combination than in the control combination.

In another embodiment, a known ligand, cofactor, substrate, or analogue thereof of the target protein is used to assay for the presence of folded target protein. The higher the fraction of protein in the folded form, the greater the amount of protein that is available to bind to a ligand that binds exclusively to the folded state. Consequently, if a protein has a known ligand, it is possible to increase or decrease the binding of the protein to the known ligand by adding a test ligand that binds another site on the protein. For example, binding of dihydrofolate reductase to methotrexate, a folic acid analogue, can be used to assess the level of folding of this enzyme.

In this approach, the ligand, cofactor, substrate, or analgoue thereof known to bind to the target protein is immobilized on a solid substrate. A solution containing the target protein and test ligand is then added. An increase or decrease in the amount of target protein that binds to the immobilized compound relative to an identical assay in the absence of test ligand indicates that the test ligand binds the target protein. The amount of target protein bound to the solid substrate can be assessed by sampling the solid substrate or by sampling the solution.

In another embodiment, the amount of unfolded target protein in a test combination is assessed by measuring protein aggregation. For proteins that unfold irreversibly, unfolded protein often forms insoluble aggregates. The extent of protein aggregation can be measured by techniques known in the art, including without limitation light scattering, centrifugation, and filtration.

In this approach, target protein and test ligand are incubated and the amount of protein aggregation is measured over time or after a fixed incubation time. The extent of protein aggregation in the test mixture is compared to the same measurement for a control assay in the absence of test ligand. If a test ligand binds a target protein, the rate of unfolding of target protein will be lower or higher than in the absence of test ligand. For measurements over time, the rate of appearance of aggregated protein will be lower or higher if the test ligand is a ligand for the target protein than if it is not. For measurements at a fixed time, there will be more or less unfolded protein and correspondingly less or more aggregated protein if the test ligand is a ligand for the target protein than if it is not. Thus, the ability of a test ligand to bind a target protein can be determined by assessing the extent of protein aggregation in the presence and absence of test ligand.

The embodiments described above are summarized in the following table.

radioimmunoassay can detect the presence or absence of a known target protein in solution or on a substrate. The above methods are described in e.g. Harlow, E. and D. Lane, *Antibodies: A Laboratory Manual*, Cold Spring Harbor Laboratories, 1988; S. F. Y. Li, *Capillary Electrophoresis*, Elsevier Press, 1993; Bidlingmeyer, *Practical HPLC Methodology and Applications*, John Wiley and Sons, Inc., 1992; and Cantor, C. R. and P. R. Schimmel, *Biophysical Chemistry*, WH Freeman and Co., 1980.

TABLE

DETERMINING FOLDED AND UNFOLDED TARGET PROTEIN

| Monitoring Method Used | Result Observed If Test Ligand Binds Target Proten |
|---|---|
| Proteolysis | |
| Protease that preferentially hydrolyzes unfolded target protein is used | More or less intact target protein in test combination than in control combination |
| Surface Binding | |
| Surface that preferentially binds unfolded target protein is used | More or less target protein unbound (in solution) to surface in test combination than in control combination |
| Antibody Binding | |
| DS antibody in solution/unfolded target protein or peptide fragment thereof on surface | More or less DS antibody bound to unfolded target protein or peptide fragment thereof on surface in test combination than in control combination |
| DS antibody in solution/antibody that recognizes folded target protein on surface | More or less target protein bound to antibody on surface in test combination than in control combination |
| NS antibody in solution/antibody that recognizes folded target protein on surface | More or less target protein bound to antibody on surface in test combination than in control combination |
| DS antibody on surface | More, or less target protein bound to DS antibody on surface in test combination than in control combination |
| NS antibody on surface | More or less target protein bound to NS antibody on surface in test combination than in control combination |
| Molecular Chaperones | |
| Chaperone on surface | More or less target protein bound to chaperone on surface in test combination than in control combination |
| Competition Assay | |
| Unfolded target protein on solid phase, target protein in solution | More or less chaperone bound to unfolded target protein on solid phase in test combination than in control |
| Chaperone in solution/antibody that recognizes folded target protein on surface | More or less target protein bound to surface-bound antibody in test combination than in control combination |
| Differential Binding to Immobilized Ligand | |
| Target protein in solution, known ligand of target protein attached to surface | More or less target protein bound to surface bound ligand in test combination than in control combination |
| Protein Aggregation | |
| Formation of aggregated protein by irreversible protein unfolding | More or less aggregated protein (higher or lower rate of formation of aggregated protein) in test combination than in control |

Protein Detection Methods

The embodiments described above require a final step for detecting and/or quantifying the level of target protein or digestion products thereof, or antibodies, in order to quantify the relative amounts of folded and unfolded target protein after exposure to test ligands. In practicing the present invention, methods known in the art are used to detect the presence or absence of protein, small peptides or free amino acids. The method used will be determined by the product (proteins, peptides, free amino acids) to be detected. For example, techniques for detecting protein size can be used to determine the extent of proteolytic degradation of the target protein e.g. gel electrophoresis, capillary electrophoresis, size exclusion chromatography, high-performance liquid chromatography, and the like. Measurement of radioactivity, fluorescence, or enzymatic activity can detect the presence or absence of products, either in solution or on a solid support. Immunological methods including e.g. ELISA and In a preferred embodiment, gel electrophoresis is used to detect the presence or absence of protein, and can further be used to detect the size of the protein. This latter method is especially useful in conjunction with proteolysis, as the presence of a greater or lesser amount of undigested target protein in the test combination than in the control combination indicates that the test ligand bound to the target protein.

The following examples are intended to illustrate the invention without limiting it thereof.

EXAMPLE 1

Methotrexate Binding Protects Dihydrofolate Reductase (DHFR) From Proteolytic Digestion by Proteinase K The following were combined and incubated at 54° C. for 5 minutes: DHFR (100 μg/ml), Proteinase K (80 μg/ml), 0.1M Tris-HCl pH 7.5, and Methotrexate at $10^{-10}$ to $10^{-4}$M.

Samples were removed and undigested DHFR was quantified by ELISA as follows:

(a) Protease incubations were diluted 50-fold with Tris-buffered saline (TBS);

(b) 50 μl diluted samples were transferred to the wells of an ELISA plate and incubated 60 minutes at room temperature;

(c) the plate wells were thoroughly washed with TBS plus 0.1% Tween-20 (TBST);

(d) 50 μl anti-DHFR rabbit serum diluted 250-fold into TBST plus 5% nonfat dry milk was added to each well and incubated 30 minutes at room temperature;

(e) plate wells were washed as in (c) above;

(f) 50 μl of goat anti-rabbit IgG alkaline phosphatase conjugate diluted 500-fold in TBST plus 5% milk was added to each well and incubated 30 minutes at room temperature;

(g) plate wells were washed as in (c); and (h) 0.1 ml of 1.0 mg/ml p-nitrophenylphosphate in 0.1% diethanolamine was added. Color development is proportional to alkaline phosphatase antibody conjugate bound.

The ELISA analysis showed that methotrexate protects DHFR from digestion at concentrations of $10^{-8}$M and higher. By the same methods, nicotinamide adenine dinucleotide phosphate (NADPH) and dihydrofolate at concentrations of $10^{-5}$M and higher were shown to inhibit proteolysis of DHFR in separate experiments.

EXAMPLE 2

Methotrexate, NADPH and Dihydrofolate Binding Protects Dihydrofolate Reductase (DHFR) From Proteolytic Digestion by Proteinase K in the Presence of a Mixture of Amino Acids The following were combined and incubated at 54° C. for 5 minutes: DHFR (2.1 μg/ml), Proteinase K (80 μg/ml), 0.1M Tris-HCl (pH 7.5), $10^{-5}$M of all 20 common amino acids and either 0 or $10^{-5}$M ligand. The ligands used were the inhibitor Methotrexate and the substrates dihydrofolate and NADPH.

Samples were removed and undigested DHFR was quantified by ELISA as follows:

(a) Protease incubations were diluted 50 fold with Tris-buffered saline (TBS);

(b) 50 μl diluted samples were transferred to the wells of an ELISA plate and incubated 60 minutes at room temperature;

(c) the plate wells were thoroughly washed with TBS plus 0.1% Tween-20 (TBST);

(d) 50 μl anti-DHFR rabbit serum diluted 250 fold into TBST plus 5% nonfat dry milk was added to each well and incubated 30 minutes at room temperature;

(e) plate wells were washed as in (c) above;

(f) 50 pl of goat anti-rabbit IgG alkaline phosphatase conjugate diluted 500 fold in TBST plus 5% milk was added to each well and incubated 30 minutes at room temperature;

(g) plate wells were washed as in (c); and (h) 0.1 ml of 1.0 mg/ml p-nitrophenylphosphate in 0.1% diethanolamine was added. Color development is proportional to alkaline phosphatase antibody conjugate bound.

The ELISA analysis showed that methotrexate and the substrates protect DHFR from digestion relative to the absence of ligands that bind to DHFR. Thus, specific binding can be detected in the presence of a complex mixture of compounds that do not bind to the target protein.

EXAMPLE 3

Methotrexate Binding Inhibits Binding of DHFR to Microliter Plates

The following were combined in a volume of 60 μl and incubated in a Falcon 3072 "tissue-culture treated" microtiter plate at 20° or 47° C.: 100 mg DHFR, 50 MM Tris-Cl (pH 7.5), and Methotrexate $10^{-10}$ to $10^{-4}$M.

50 μl of each sample was then transferred to the wells of an ELISA plate, and the DHFR that remained in solution was quantified by ELISA as follows:

(a) The 50 μl samples were incubated for 60 minutes at room temperature;

(b) the plate wells were thoroughly washed with TBS plus 0.1% Tween-20 (TBST);

(c) 50 μl anti-DHFR rabbit serum diluted 250-fold into TBST plus 5% nonfat dry milk was added to each well and incubated 30 minutes at room temperature;

(d) plate wells were washed as in (c) above;

(e) 50 μl of goat anti-rabbit IgG alkaline phosphatase conjugate diluted 500-fold in TBST plus 5% milk was added to each well and incubated 30 minutes at room temperature;

(f) plate wells were washed as in (b); and (g) 0.1 ml of 1.0 mg/ml D-nitrophenylphosphate in 0.1% diethanolamine was added. Color development is proportional to alkaline phosphatase antibody conjugate bound.

The ELISA analysis revealed that methotrexate inhibits DHFR binding to the Falcon 3072 plate at concentrations of $10^{-7}$M and above.

EXAMPLE 4

Inhibition or Enhancement of Unfolded-Specific Antibody Binding (1) ELISA plates are coated by incubation for 60 minutes with the following mixture: 4 μg/ml irreversibly denatured target protein or peptide fragments thereof in Tris-buffered Saline (10 mM Tris-Cl, pH 7.5, 0.2M NaCl; TBS).

(2) The plates are washed 3 times with TBS plus 0.1% Tween-20 (TBST).

(3) The following mixture (total volume 50 μl) is incubated in the coated wells of the microliter plate for 60 minutes:

(a) Antibody specific for the unfolded state of the target protein at a sufficient concentration to give 50% of maximal binding (in the absence of competing target protein).

(b) Target protein at a concentration sufficient to achieve 90% inhibition of antibody binding to the plate. The appropriate target protein concentration differs for each target protein. The concentration depends, in part, on the stability of the folded form of the target protein. In some cases it may be desirable to reduce the stability of the target protein by elevated temperature, inclusion of chemical protein-denaturing agents, or introduction of destabilizing amino acid substitutions in the target protein.

(c) $10^{-9}$ to $10^{-5}$M test ligands (d) 5% nonfat dry milk in TBST (4) The plates are washed 3 times with TBST.

(5) 50 µl of goat anti-IgG alkaline phosphatase conjugate at an appropriate dilution are added in TBST plus 5% nonfat dry milk and incubated for 30 minutes at room temperature.

(6) Plates are washed 3 times with TBST.

(7) 0.1 ml of 1.0 mg/ml D-nitrophenylphosphate in 0.1% diethanolamine are added and the amount of color development recorded by means of an ELISA plate reader.

ELISA analysis will reveal more or less antibody bound to the plate when successful test ligand-target protein binding has occurred than in the absence of such binding.

EXAMPLE 5

Inhibition or Enhancement of Chaperone Binding (1) ELISA plates are coated by incubation for several hours with 4 µg/ml chaperone in TBS.

(2) The plates are washed 3 times with TBST.

(3) The following mixture (total volume 50 µl) is then incubated in the coated wells of the microtiter plate 10 for 60 minutes:

(a) Target protein at a concentration sufficient to saturate about 50% of the available binding sites present on the chaperone proteins. Denaturing conditions may be used in cases where the folded form of the target protein is otherwise too stable to permit appreciable binding to chaperones.

(b) $10^{-9}$ to $10^{-5}$M test ligands in TBST (4) Aliquots of the well solutions are transferred to wells of a new ELISA plate and incubated for 60 minutes at room temperature.

(5) The plate wells are washed 3 times with TBST.

(6) 50 µl antibody specific for the target protein at the appropriate dilution in TBST, plus 5% nonfat dry milk, are added to each well and incubated 30 minutes at room temperature.

(7) The plate wells are washed 3 times with TBST.

(8) 50 µl of goat anti-rabbit IgG alkaline phosphatase conjugate at an appropriate dilution in TBST plus 5% nonfat dry milk are added to each well and incubated 30 minutes at room temperature.

(9) The plate wells are washed 3 times with TBST.

(10) 0.1 ml of 1.0 mg/ml p-nitrophenylphosphate in 0.1% diethanolamine will be added. Color development (proportional to alkaline phosphatase antibody conjugate bound) is monitored with an ELISA plate reader.

ELISA analysis will reveal target protein in the solution at higher or lower concentration when test ligand-target protein binding has occurred than when it has not.

EXAMPLE 6

Enhancement or Inhibition of Binding to a Known Ligand (1) The following mixture (total volume 50 µl) is incubated in the coated wells of the microliter plate for 60 minutes:

(a) Ligand known to bind to the target protein, covalently attached to solid beads such as Sephadex. This ligand can be a small molecule or a macromolecule.

(b) Target protein at a concentration well below saturation of the ligand and such that only 10% of the protein binds to the ligand sites. The solution conditions are such that most of the target protein is present in the denatured state.

(c) $10^{-9}$ to $10^{-5}$M test ligands (d) in TBST plus necessary denaturant, such as urea.

(2) Aliquots of the well supernatant (free of beads) are transferred to wells of a new ELISA plate and incubated for 60 minutes at room temperature.

(3) The plate wells are washed 3 times with TBST.

(4) 50 µl antibody specific for the target protein at the appropriate dilution in TBST, plus 5% nonfat dry milk, are added to each well and incubated 30 minutes at room temperature.

(5) The plate wells are washed 3 times with TBST.

(6) 50 pl of goat anti-rabbit IgG alkaline phosphatase conjugate at an appropriate dilution in TBST plus 5% milk are added to each well and incubated 30 minutes at room temperature.

(7) The plate webs are washed 3 times with TBST.

(8) 0.1 ml of 1.0 mg/ml p-nitrophenylphosphate in 0.1% diethanolamine are added. Color development (proportional to alkaline phosphatase antibody conjugate bound) is monitored with an ELISA plate reader.

ELISA analysis will reveal a higher or lower concentration of target protein in the solution when successful test ligand-target protein binding has occurred.

EXAMPLE 7

Low throughput Assay for Carbonic Anhydrase Ligands

Ligand binding to carbonic anhydrase I (Sigma) was tested using proteolysis as a probe of target protein folding, and denaturing gel electrophoresis was used as a method for detection of intact protein remaining after digestion with proteases.

To validate the assay, acetazolamide, a known ligand of carbonic anhydrase, was tested. Though acetazolamide is a known inhibitor of carbonic anhydrase activity, these experiments make no use of that property, and do not measure the enzymatic activity of the protein. In addition, the sensitivity of the method to interference by a natural product extract was examined.

Reaction mixtures contained 13.3 µg/ml carbonic anhydrase, 0.05M Tris-HCl pH 7.5, 0.01M calcium acetate, 2.5 µg/ml proteinase K, 10% DMSO and acetazolamide (Sigma) in concentrations ranging from 0.0 to 1.0 mM. The reactions were incubated at 54° C. for 15 minutes, and then chilled on ice. Phenyl methyl sulfonyl fluoride (PMSF) was then added from a 20 mM stock solution in ethanol to a final concentration of 1 mM, and EDTA was added from a 0.5M stock solution to a final concentration of 20 mM. 0.01 ml of SDS loading buffer (10% sodium dodecyl sulfate (SDS), 0.5M Dithiothreitol, 0.4M Tris-HCl buffer, pH 6.8, 50% Glycerol) was added and samples were heated at 95° C. for 3 minutes. Samples were analyzed by SDS-polyacrylamide gel electrophoresis using a 4–15% polyacrylamide (BioRad) gradient gel, which was then stained with Coomassie Blue dye.

As shown in FIG. 1, binding of the known ligand acetazolamide to carbonic anhydrase resulted in stabilization of carbonic anhydrase against proteolysis by proteinase K at $1\times10^{-5}$M acetazolamide. The dissociation constant for this interaction has been reported to be $2.6\times10^{-6}$M (Matsumoto, K. et. al. (1989), *Chem. Pharm. Bull*, 37:1913–1915).

Figure 2:
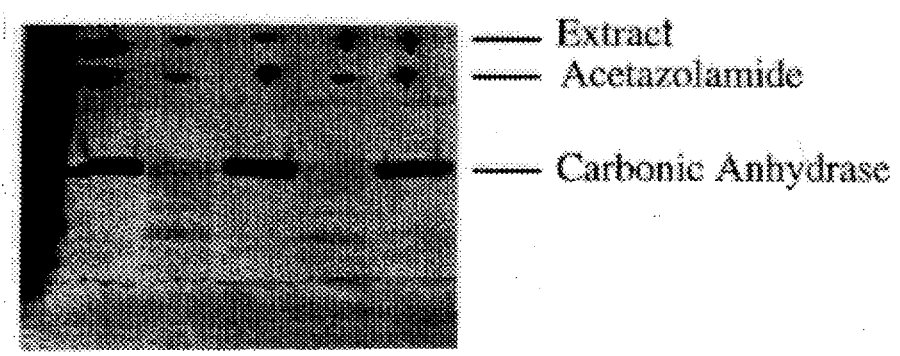
FIG. 2 shows an SDS-polyacrylamide gel profile of carbonic anhydrase after proteolysis in the absence and presence of 1.0 mM acetazolamide, in the absence and presence of a fungal extract.

A fungal methanol extract was included in reactions that were otherwise identical to that described above such that the final concentration of an added small molecule would be equal to its concentration in the source culture. The presence of extract neither induced a false signal nor diminished the response to 1.0 mM acetazolamide (FIG. 2.)

EXAMPLE 8

Low Throughput Assay for HIV Rev Protein

Reaction mixtures (0.03 ml total volume) contained 30 µg/ml HIV Rev protein that had been produced in *E. coli*, 0.05M Tris-HCl, pH 7.5, 0.01M calcium acetate, 2.5 µg/ml proteinase K, 10% DMSO, and varying amounts of tRNA as a known ligand. The reactions were incubated on ice for 15 minutes. After addition of PMSF and EDTA as described in Example 7 above, samples were prepared for gel electrophoresis and analyzed as described in Example 7.

The results showed that in the absence of tRNA, Rev protein is almost completely degraded by proteinase K under these conditions. In the presence of tRNA, however, a lower-molecular weight fragment of the protein is stabilized against proteolysis. Thus, binding of a known ligand to HIV Rev protein is detectable using the methods of the present invention.

EXAMPLE 9

High-throughput Screening of Ligands for Human Neutrophil Elastase

In practicing the present invention, the ability to perform the binding assay on large numbers of compounds is critical to its utility in discovering compounds with potential pharmaceutical utility. Two different approaches have been successfully implemented in a high-throughput screening mode and each of these has been applied to two target proteins: human neutrophil elastase (HNE) and human hemoglobin, both hemoglobin A (HbA) and hemoglobin S (HbS) (described in Example 10 below).

Notably, these target proteins differ from one another in a number of important respects: HbS is an intracellular, tetrameric protein that contains a prosthetic group critical to its function. It is known to exist in two conformations with different structural and functional properties. In contrast, HNE is monomeric, lacks a prosthetic group, and is secreted. HNE has an enzymatic activity (proteolysis) and does not appear to undergo any global conformational changes.

For high-throughput screening with both of these target proteins, proteolysis is used as the probe of target protein folding. The two high-throughput modes differ in the methods used for detection of residual target protein following proteolysis. The two detection methods are 1) capture of radiolabeled protein on nitrocellulose filters followed by quantitation of bound radioactivity and 2) measurement of protein by enzyme linked immunosorbent assay (ELISA.) Each of these methods was used successfully with both hemoglobin and HNE.

A) Nitrocellulose Binding of Radiolabelled HNE:

0.1 mg HNE (Elastin Products) was labelled by reaction with $^{125}$I-Sodium Iodide (Amersham) in the presence of Iodogen (Pierce) according to manufacturer's protocols (Pierce). Reaction mixtures were prepared in a final volume of 0.05 ml containing radiolabelled HNE (20,000 cpm, corresponding to approximately 10 µg), 0.025 mg/ml Bovine Serum Albumin, 50 mM Tris-HCl, pH 7.5, 10 mM calcium acetate, 2.5 µg/ml thermolysin (Boeringer Mannheim), 2.5 µg/ml proteinase K (Merck), 10% DMSO, and the test compound at a concentration of 200 µM. Control mixtures were identical, except that the test compound was omitted.

The mixtures were incubated at 20° C. for 15 minutes, then at 65° C. for 30 minutes, after which they were placed on ice. 0.12 ml 50 mM sodium acetate buffer, pH 4.5, was then added to each mixture. After an additional 15 minute incubation on ice, the samples were filtered through nitrocellulose membrane sheets using the Schleicher and Schuell Minifold. Each well of the apparatus was then washed once with 0.2 ml 50 mM sodium acetate buffer, pH 4.5, and twice with 0.5 ml 50 mM sodium phosphate, pH 5.5, containing 2.0% SDS and 1.0% Triton X-100. After drying the filter, bound radioactivity was determined by scintillation counting using the Wallac MicroBeta apparatus.

Figure 3:
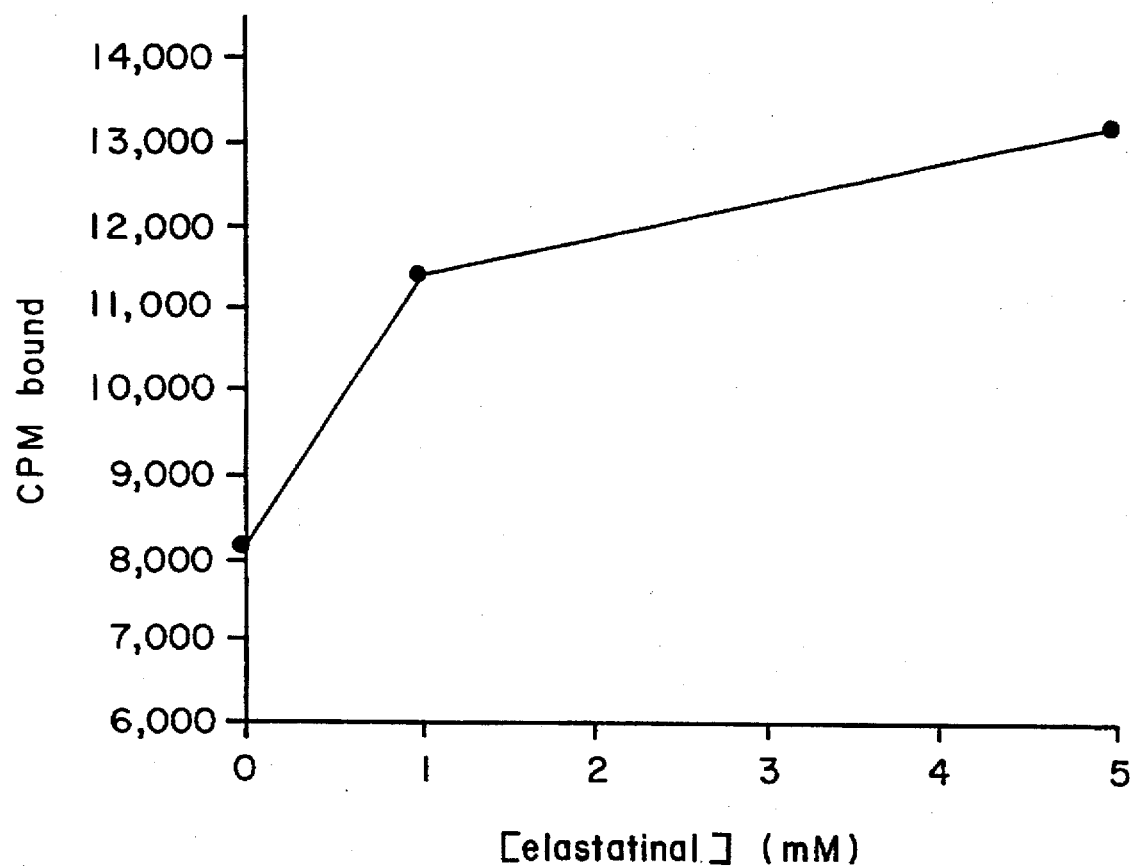
FIG. 3 shows a graph representing a titration of the binding of radiolabelled human neutrophil elastase to nitrocellulose filters after proteolysis in the absence and presence of increasing concentrations of elastatinal.

To validate the assay, a known ligand for HNE, elastatinal, was included in the assay at concentrations ranging from 1–5 mM. As shown in FIG. 3, inclusion of elastatinal increased the retention of labelled HNE on the nitrocellulose filters, indicating that it protected HNE from proteolysis.

B) ELISA Quantitation of HNE:

Reaction mixtures in final volume of 0.05 ml contained 2 µg/ml HNE, 0.020 mg/ml Bovine Serum Albumin, 50 mM Tris-HCl, pH 7.5, 10 mM calcium acetate, 7.5 µg/ml therinolysin (Boeringer Mannheim), 7.5 µg/ml proteinase K (Merck), 10% DMSO, and the test compound at 20 or 200 µM concentration. Control mixtures were identical except that the test compound was omitted. The mixtures were incubated at 20° C. for 15 minutes, then at 63° C., 30 minutes then placed on ice.

0.1 ml of rabbit anti HNE antibody (Calbiochem) at a dilution of 1:10,000 in TBST (10 mM Tris-HCl, pH 7.5, 0.15M NaCl, 0.05% Tween-20) containing 5% nonfat dry milk (Carnation) was then added to each reaction. After 10 minutes incubation at room temperature, the mixtures were transferred to 96-well Immulon-4 plates (Dynatech) that had been coated with HNE by overnight incubation with 0.1 ml per well of 0.2 µg/ml HNE in 50 mM Sodium Borate buffer, pH 8.5, and 3 mM sodium azide and then washed thoroughly with TBST. The plates were then incubated at room temperature for one hour, after which they were thoroughly washed with TBST. 0.1 ml of alkaline phosphatase-conjugated goat anti-rabbit IgG antibody (Calbiochem) diluted 1:1000 in TBST containing 5% nonfat dry milk was added to each well, and the plates were incubated at room temperature for 1–2 hours. The plates were then washed thoroughly with TBST and finally with TBST lacking Tween. 0.1 ml per ml of p-nitrophenylphosphate (0.5 mg/ml) in 1× diethanolamine substrate buffer (Pierce) was added to each well. Plates were incubated at room temperature until color developed, after which the absorbance of each well at 405 nm was measured using a BioRad 3550-UV microplate reader.

Figure 4:
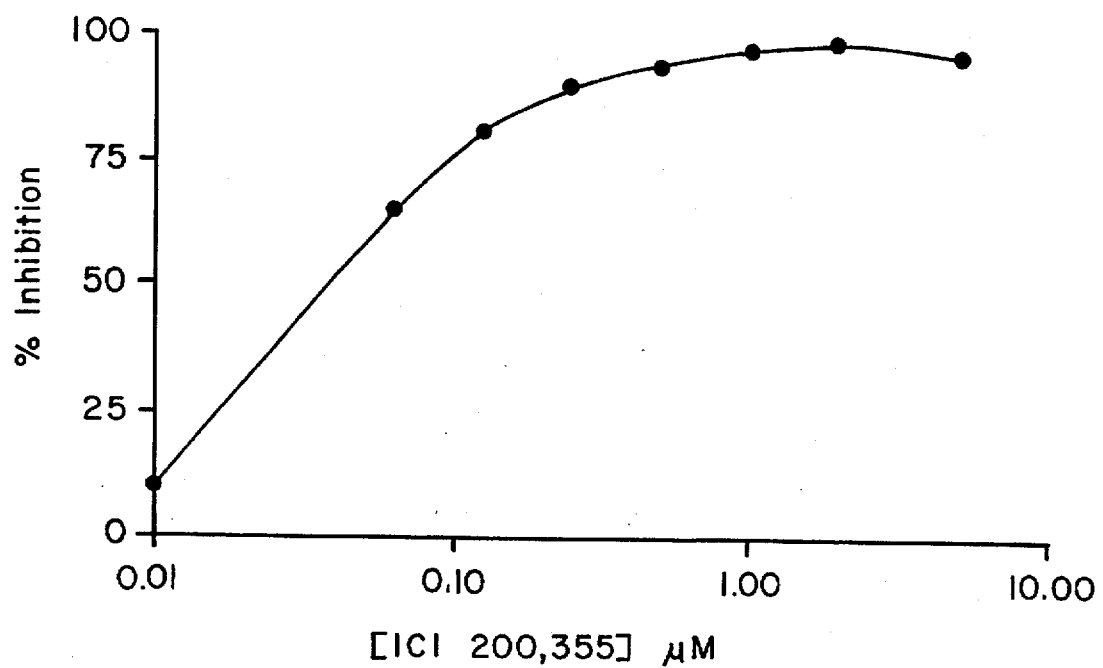
FIG. 4 shows a graph representing a titration of the ELISA detection of human neutrophil elastase after proteolysis in the presence of increasing concentrations of IC 200,355.

To validate the assay, a known ligand for HNE, ICI 200,355, was included in the assay at concentrations ranging from 0.01–10 µM. As shown in FIG. 4, inclusion of the ligand caused an inhibition of antibody binding to the plate, indicating an increased level of immunoreactive HNE in the reaction mixtures.

Figure 5:
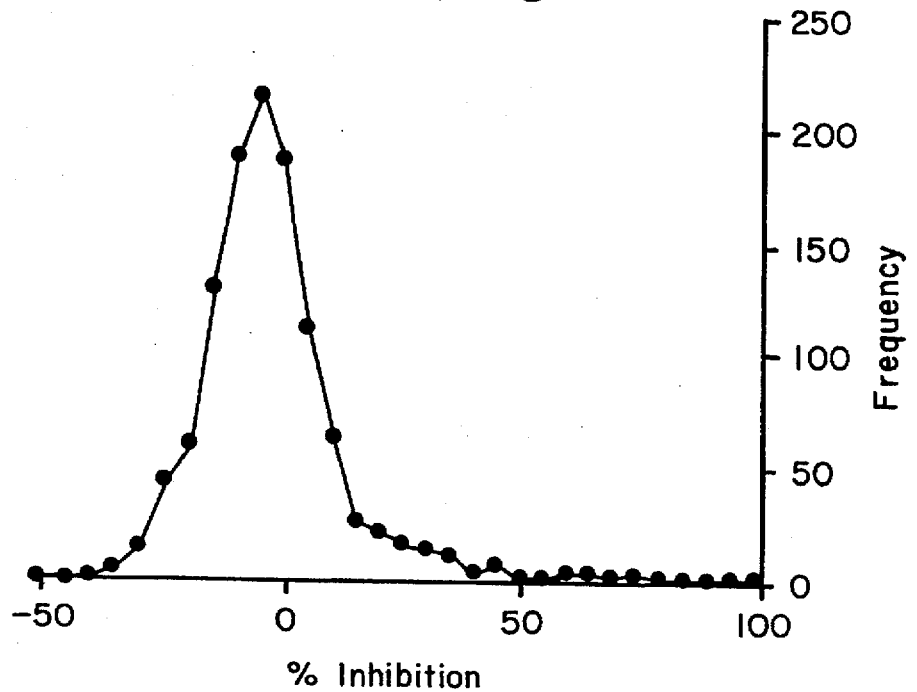
FIG. 5 shows a graph representing the distribution of test ligands identified as ligands of human neutrophil elastase.
Figure 6:
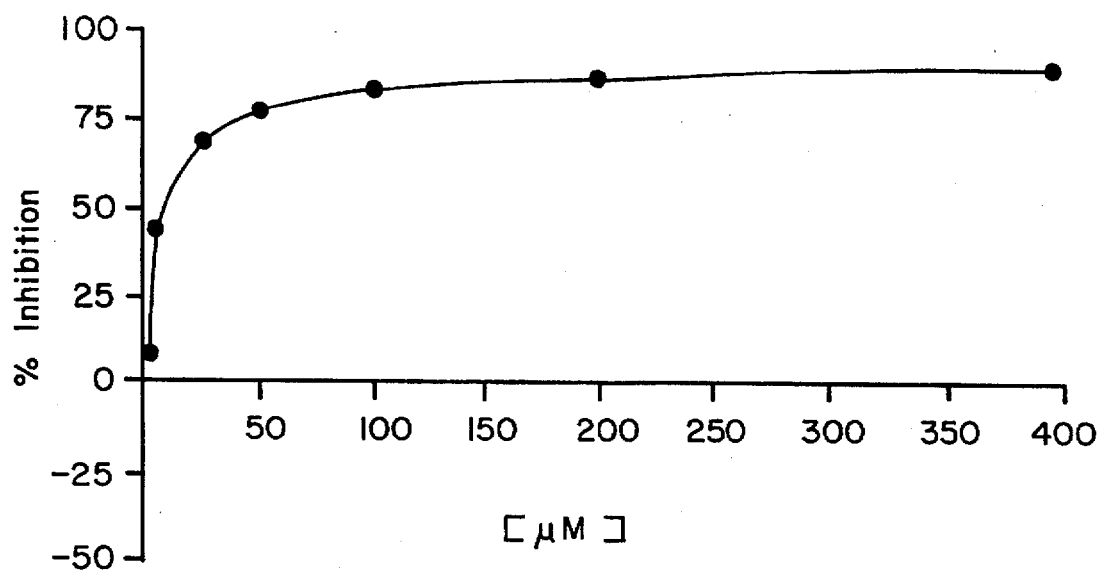
FIG. 6 shows a graph representing the titration of a ligand for human neutrophil elastase.

C) Results of High-Throughput Screening:

3,600 compounds have been screened for interaction with HNE using proteolysis and ELISA detection as above (FIG. 5). Of these, 24 inhibited proteolysis of HNE by proteinase K to an extent of 50% or more when assayed at a concentration of 20 µM (positive hit compounds.) An additional 6 compounds were found to increase the extent of proteolysis at least two-fold when tested at 20 µM (negative hit compounds.) The concentration dependence of the effects of hit compounds was measured. Hit compounds showed half maximal effects at concentrations as low as 8 µM; one example is shown in FIG. 6. Maximal inhibition was usually, but not always, nearly 100%.

Figure 7:
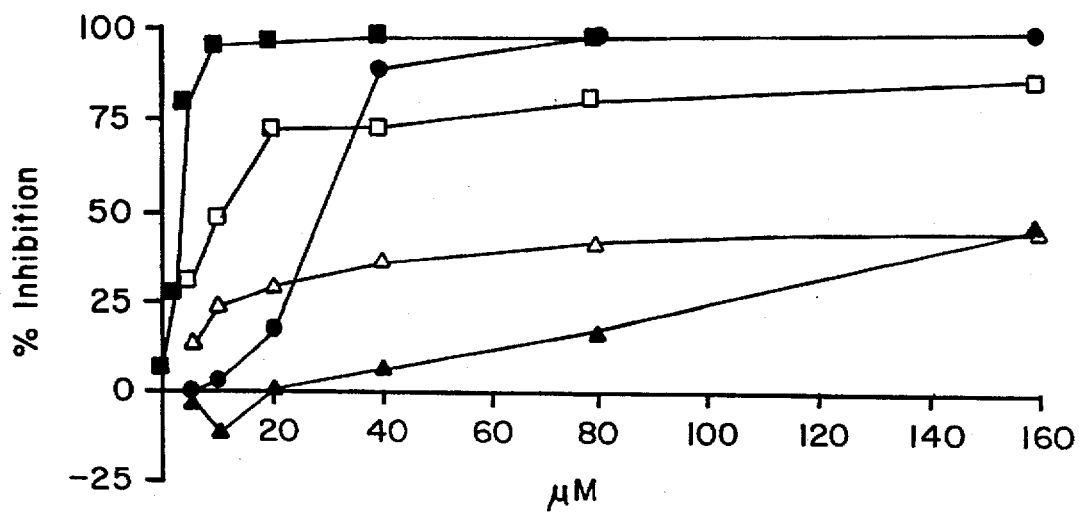
FIG. 7 shows a graph representing the titration of five ligands for their ability to inhibit the enzymatic activity of human neutrophil elastase.

The hit compounds were assayed for their ability to inhibit the enzymatic activity of HNE. Since compounds identified in the binding assay may bind anywhere on the protein surface, only a small fraction would be expected to inhibit the enzymatic activity of HNE. The compounds were tested as inhibitors of the proteolysis of Suc-(Ala)$_3$-pNA (Elastin Products), a chromogenic synthetic substrate, according to the method of Bieth, J, Spiess, B. and Wermuth, C. G. (1974, *Biochemical Medicine*, 11: 350–357.) Two positive hit compounds and one negative hit compound inhibit the proteolytic activity of HNE significantly in these assays (FIG. 7).

EXAMPLE 10

High-throughput Screening of Ligands for Human Hemoglobin

A) Nitrocellulose Binding of Radiolabelled Hemoglobin:

0.2 mg HbS or HbA (Sigma) was radiolabelled by reaction with 1 mCi $^{125}$I-Bolton-Hunter reagent (Amersham) in 100 mM sodium borate buffer, pH 8.5, on ice for one hour. Labelling was stopped by addition of borate buffer containing 200 mM glycine. The mixture was then fractionated by size on an execellulose GF-5 column (Pierce) in 50 mM sodium phosphate buffer, pH 7.5, containing 0.25% gelatin.

For the binding assay, reaction mixtures in a final volume of 0.05 ml contained radiolabelled hemoglobin (20,000 CPM), 0.063 mg/ml unlabelled hemoglobin, 0.034 mg/ml Bovine Serum Albumin, 50 mM Tris-HCl, pH 7.5, 10 mM calcium acetate, 2.5 µg/ml thermolysin (Boeringer Mannheim), 2.5 µg/ml proteinase K (Merck), 10% DMSO, and test compound. Control mixtures were identical, except that the test compound was omitted. The mixtures were incubated at 20° C. for 15 minutes, then 40° C. for 30 minutes and then placed on ice. 0.12 ml 50 mM sodium acetate buffer, pH 4.5, was then added to each mixture. After an additional 15 minute incubation on ice, the samples were filtered through nitrocellulose membrane sheets using the Schleicher and Schuell Minifold. Each well of the apparatus was then washed once with 0.2 ml 50 mM sodium acetate buffer, pH 4.5, twice with 0.5 ml of 50 mM sodium phosphate buffer, pH 5.5, containing 2.0% SDS and 1.0% Triton X-100. After drying the filter, bound radioactivity was determined by scintillation counting using the Wallac MicroBeta apparatus.

Figure 8:
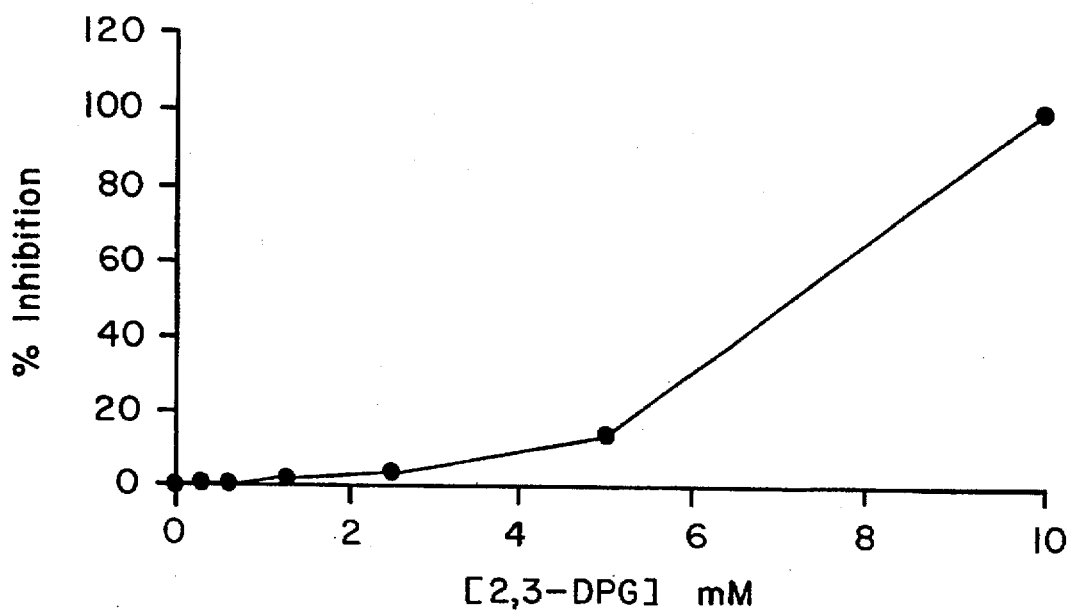
FIG. 8 shows a graph representing a titration of the binding of human hemoglobin to nitrocellulose filters after proteolysis in the absence or presence of increasing concentrations of 2,3-diphosphoglycerate.

To validate the assay, a known ligand for hemoglobin, 2,3-diphosphoglycerate, was included in the reaction mixture at concentrations ranging from $10^{-5}$ to $10^{-1}$M. As shown in FIG. 8, 2,3-diphosphoglycerate significantly increased the filter retention of hemoglobin.

B) ELISA Quantitation of Hemoglobin:

Reaction mixtures in a final volume of 0.05 ml contained 0.063 mg/ml Hemoglobin, 0.034 mg/ml Bovine Serum Albumin, 50 mM Tris-HCl, pH 7.5, 10 mM calcium acetate, 7.5 µg/ml thermolysin (Boeringer Mannheim), 7.5 µg/ml proteinase K (Merck), 10% DMSO, and the test compound at 20 or 200 µM concentration. Control reactions were identical, except that the test compound was omitted.

The mixtures were incubated at 20° C. for 15 minutes, then at 44° C. for 30 minutes, and then placed on ice. To each mixture was then added 0.05 ml 0.1M sodium borate buffer containing 20 mM EDTA and 1 mM PMSF. After 10 minutes incubation on ice, the mixtures were transferred to uncoated 96-well Immuulon-4 plates (Dynatech). The plates were then incubated at 4° C. overnight to allow binding of the protein to the plate. The plates were washed thoroughly with TBST, and 0.1 ml of rabbit anti-human hemoglobin antibody (Calbiochem) dilute 1:500 was added to each well. The plates were incubated at room temperature for one hour, then thoroughly washed with TBST. Next 0.1 ml of alkaline phosphatase conjugated goat anti rabbit IgG antibody (Calbiochem) diluted 1:1000 in TBST plus 5% nonfat dry milk was added to each well and the plates were incubated at room temperature 1–2 hours. The plates were then washed thoroughly with TBST and finally with TBST lacking Tween. 0.1 ml per ml of p-nitrophenylphosphate (0.5 mg/ml) in 1× diethanolamine substrate buffer (Pierce) was added to each well. Plates were incubated at room temperature until color developed and the absorbance of each well at 405 nm was measured using a BioRad 3550-UV microplate reader.

Figure 9:
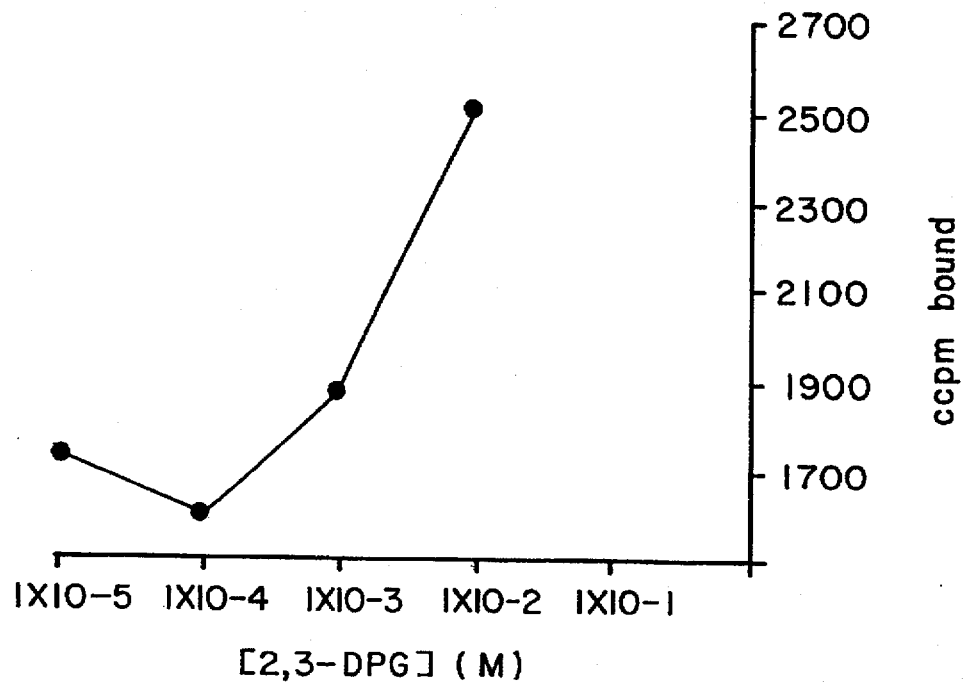
FIG. 9 shows a graph representing a titration of the ELISA detection of human hemoglobin after proteolysis in the presence of increasing concentrations of 2,3-diphosphoglycerate.

To validate the assay, a known ligand for hemoglobin, 2,3,-diphosphoglycerate, was included in the reaction. As shown in FIG. 9, this compound increased the detection of immunoreactive hemoglobin.

Figure 10:
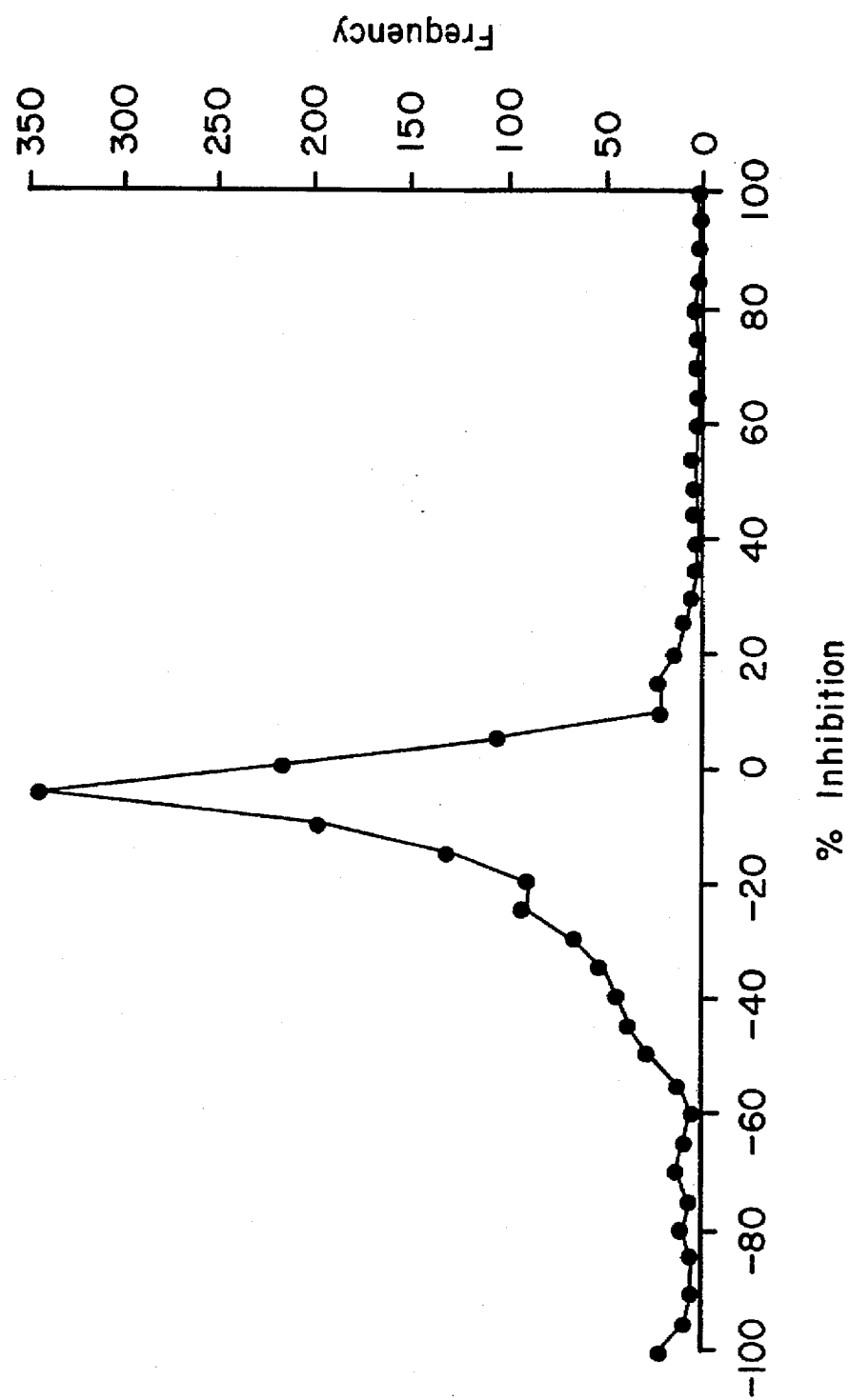
FIG. 10 shows a graph representing the distribution of test ligands identified as ligands of human hemoglobin S.

C) Results of High-throughput Screening:

4,000 compounds have been screened for interaction with HbS using proteolysis and ELISA detection as above (FIG. 10). Of these, 23 were found to inhibit proteolysis to an extent of 20% or more when assayed at a concentration of 20 µM (positive hit compounds.)

Figure 11:
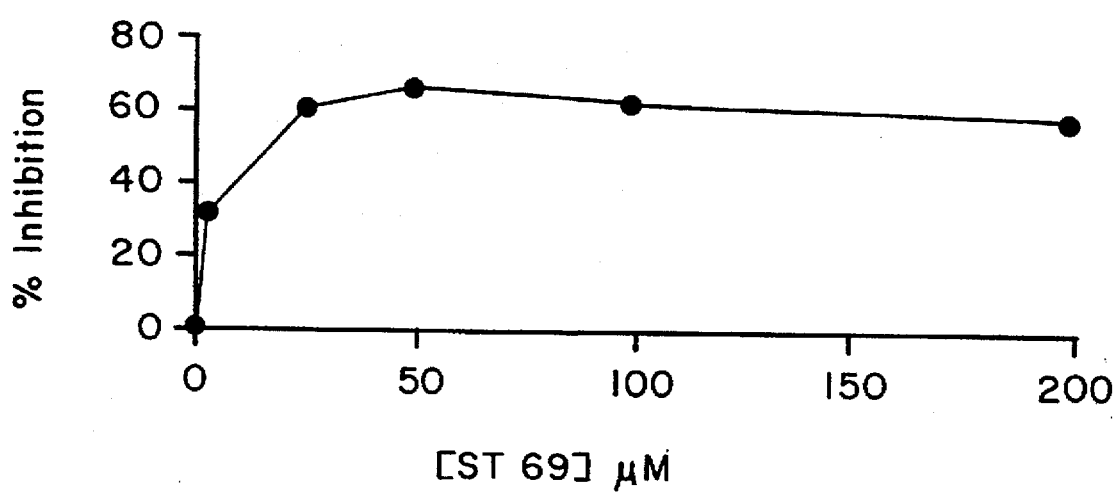
FIG. 11 shows a graph representing the titration of a ligand for human hemoglobin.

The concentration dependence of the effects of hit compounds was measured. Hit compounds showed half maximal effects at concentrations ranging as low as 2.0 µM (For example, see FIG. 11).

What is claimed is:

1. A method for identifying a ligand that binds a predetermined target protein, which comprises:

(a) selecting as test ligands a plurality of compounds not known to bind to the target protein;

(b) incubating each of said test ligands and the target protein to produce a test combination;

(c) incubating the target protein in the absence of a test ligand to produce a control combination;

(d) treating the test and control combinations to cause a detectable fraction of the target protein to unfold to a measurable extent;

(e) determining the fraction of target protein in each treated combination that exists in an unfolded state, a folded state, or both;

(f) comparing the determination made in step (e) between the test and control combinations, wherein if the target protein is present in the folded state to a greater extent in the test combination than in the control combination, the test ligand is a ligand that binds to the target protein; and (g) repeating steps (b)–(f) with a plurality of said test ligands until a ligand that binds to the target protein is identified.

2. The method of claim 1, wherein the ligand binds to surface or internal amino acid residues or conformational domains of the target protein.

3. The method of claim 1, wherein the treating step comprises at least one of altering the temperature, adding denaturing compounds, and combinations thereof.

4. The method of claim 3, wherein the denaturing compounds are selected from the group consisting of urea, guanidinium and salts thereof, detergents, and combinations thereof.

5. The method of claim 1, wherein the determining step comprises subjecting the test and control combinations to at least one of proteolysis; antibody binding; surface binding; molecular chaperone binding; binding to a known ligand, cofactor, substrate, or analogue thereof of the target protein; circular dichroism spectroscopy; ultraviolet spectroscopy; fluorescence spectroscopy; calorimetry; and combinations thereof.

6. The method of claim 5, wherein proteolysis comprises the steps of:

(i) contacting the test and control combinations with one or more proteases under conditions that result in preferential degradation of the target protein in its unfolded state, and (ii) measuring the fraction of the target protein that remains undegraded in the test and control combinations, the ligand being any test ligand that causes an increase or decrease in said fraction in the test combination relative to said fraction in the control combination.

7. The method of claim 5, wherein surface binding comprises the steps of:

(i) exposing the test and control combinations to a surface under conditions in which the surface preferentially binds the target protein in its unfolded state, and (ii) determining the fraction of the target protein bound to the surface in the test and control combinations, the ligand being any test ligand that causes an increase or decrease in said fraction in the test combination relative to said fraction in the control combination.

8. The method of claim 5, wherein said binding to a known ligand, cofactor, substrate, or analogues thereof comprises the steps of:

(i) immobilizing the known ligand, cofactor, substrate, or analgoue thereof on a solid support;

(ii) exposing the solid support to the test and control combinations, under conditions in which the target protein in its folded state binds to the support; and (iii) determining the fraction of the target protein bound to the support in the test and control combinations, the ligand being any test ligand that causes an increase or decrease in said fraction in the test combination relative to said fraction in the control combination.

9. The method of claim 5, wherein antibody binding comprises exposing the test and control combinations to antibodies specific to the folded form of the target protein or to antibodies specific to the unfolded form of the target protein, wherein the antibodies are in solution or bound to a solid support.

10. The method of claim 9, further comprising the steps of:

(i) coating a solid support with the target protein in its unfolded state;

(ii) incubating the test and control combinations with an antibody specific to the unfolded state of the target protein;

(iii) exposing the mixture formed in (ii) to the coated support; and (iv) determining the amount of antibody bound to the support, the ligand being any test ligand that causes an increase or decrease in the amount of bound antibody in the test combination relative to the amount of bound antibody in the control combination.

11. The method of claim 9, further comprising the steps of:

(i) coating a solid support with an antibody specific to the unfolded state of the target protein;

(ii) exposing the support to the test and control combinations; and (iii) determining the amount of target protein bound to the support, the ligand being any test ligand that causes an increase or decrease in the amount of bound target protein in the test combination relative to the amount of bound target protein in the control combination.

12. The method of claim 5, wherein molecular chaperone binding comprises the steps of:

(i) coating a solid support with a molecular chaperone protein that binds the target protein in its unfolded state;

(ii) exposing the test and control combinations to the coated support; and (iii) determining the amount of target protein bound to the support, the ligand being any test ligand that causes an increase or decrease in said amount in the test combination relative to said amount in the control combination.

13. The method of claim 5, wherein molecular chaperone binding comprises the steps of:

(i) coating a solid support with the target protein in its unfolded state;

(ii) incubating the test and control combinations with a molecular chaperone that binds the target protein in its unfolded state, forming a mixture;

(iii) exposing the mixture to the coated support; and (iv) determining the amount of molecular chaperone bound to the support, the ligand being any test ligand that causes an increase or decrease in said amount in the test combination relative to said amount in the control combination.

14. The method of claim 5, comprising the steps of:

(i) coating a solid support with antibodies specific to the target protein in its folded state;

(ii) incubating the test and control combinations with a molecular chaperone that binds the target protein in its unfolded state, forming a mixture;

(iii) exposing the mixture to the coated support; and (iv) determining the amount of target protein bound to the support, the ligand being any test ligand that causes an increase or decrease in said amount in the test combination relative to said amount in the control combination.

15. A method for identifying a ligand that binds a target protein, comprising the steps of:

(i) selecting as test ligands a plurality of compounds not known to bind to the target protein;

(ii) incubating each of said test ligands with the target protein to produce a test combination (iii) incubating the target protein in the absence of a test ligand to produce a control combination;

(iv) subjecting the test and control combinations to increased temperature, thereby causing a detectable fraction of said target protein to exist in an unfolded state;

(v) incubating the test and control combinations with one or more proteases under conditions that preferentially degrade the target protein in its unfolded state; and (vi) measuring the fraction of the protein that remains undegraded in the test and control combinations, the ligand being any test ligand that causes an increase or decrease in said fraction in the test combination relative to said fraction in the control combination.

16. The method of claim 15, wherein the protein is selected from the group consisting of carbonic anhydrase, human neutrophil elastase, human hemoglobin, dihydrofolate reductase, and HIV Rev protein.

17. The method of claim 15, wherein the proteases are selected from the group consisting of proteinase K, thermolysin, and combinations thereof.

18. The method of claim 15, wherein the determining step comprises subjecting the test and control combinations to denaturing polyacrylamide gel electrophoresis.

19. A method for identifying a ligand that binds human neutrophil elastase, comprising the steps of:
(i) selecting as test ligands a plurality of compounds not known to bind to the target protein;
(ii) incubating the elastase in the presence of test ligand to produce a test combination, and incubating the elastase in the absence of a test ligand to produce a control combination;
(iii) treating the test and control combinations with Proteinase K and thermolysin, under conditions of increased temperature; and
(iv) measuring the fraction of the elastase that remains undegraded in the test and control combinations,
the ligand being any test ligand that causes an increase or decrease in said fraction in the test combination relative to said fraction in the control combination.

20. A method of identifying a ligand of a target protein, comprising the steps of:
a) selecting as test ligands a plurality of compounds not known to bind to the target protein;
b) incubating each of said test ligands and a target protein under conditions appropriate for the target protein to alternate between its folded state and its unfolded state and appropriate for binding of the target protein to a ligand of the target protein, thereby producing a test combination;
c) determining the extent to which the target protein occurs in the folded state, the unfolded state or both in the test and control combinations;
d) comparing the determination made in (c) between test and control combinations, wherein if the target protein is present in the folded state to a greater extent in the test combination than in the control combination, the test ligand is a ligand of the target protein; and
e) repeating steps (b)–(d) with a plurality of said test ligands until a ligand that binds the target protein is identified.

21. The method of claim 20, wherein in step (b) and in step (c), determining the extent to which target protein occurs in the folded state, the unfolded state or both is carried out by a method selected from the group consisting of: proteolysis, antibody binding, surface binding, molecular chaperone binding and differential binding to immobilized ligand.

22. The method of claim 21, wherein in step (b) the extent to which the target protein occurs in the folded state, the unfolded state or both and in step (c) the extent to which the target protein occurs in the corresponding state is determined by proteolysis and comprises the steps of:
(i) incubating the target protein, the test ligand and one or more proteases which preferentially degrade target protein in its unfolded state, whereby the target protein in its unfolded state is degraded preferentially; and
(ii) measuring the fraction of the target protein degraded or the fraction of the target protein remaining in an intact state, wherein if the fraction of targets protein remaining in the intact state in the test combination is greater than in the control combination, the test ligand is a ligand of the target protein.

23. A method of identifying a ligand of a target protein, comprising the steps of:
a) selecting as test ligands a plurality of compounds not known to bind to the target protein;
b) incubating each of said test ligands and a target protein under conditions appropriate for the target protein to irreversibly unfold to an appropriate extent and appropriate for binding of the target protein to a ligand of the target protein, thereby producing a test combination;
(c) determining the extent to which the target protein occurs in the folded state, the unfolded state or both in the test and control combinations;
(d) comparing the determination made in (c) between test and control combinations, wherein if the target protein is present in the folded state to a greater extent in the test combination than in the control combination, the test ligand is a ligand of the target protein; and
(e) repeating steps (b)–(d) with a plurality of said test ligands until a ligand that binds to the target protein is identified.

24. The method of claim 23, wherein in step (b) and in step (c), determining the extent to which target protein occurs in the folded state, the unfolded state or both is carried out by a method selected from the group consisting of: proteolysis, antibody binding, surface binding, molecular chaperone binding, differential binding to immobilized ligand and differential formation of aggregated protein.

25. The method of claim 24, wherein in step (b) the extent to which the target protein occurs in the folded state, the unfolded state or both and in step (c) the extent to which the target protein occurs in the corresponding state is determined by proteolysis and comprises the steps of:
(i) incubating the target protein, the test ligand and one or more proteases which preferentially degrade target protein in its unfolded state, whereby the target protein in its unfolded state is degraded preferentially; and
(ii) measuring the fraction of the target protein degraded or the fraction of the target protein remaining in an intact state, wherein if the fraction of targets protein remaining in the intact state in the test combination is greater than in the control combination, the test ligand is a ligand of the target protein.

26. A method for rapid, large-scale screening to identify a ligand that binds to a predetermined target protein, comprising the steps of:
(a) selecting as test ligands a plurality of compounds not known to bind to the target protein;
(b) incubating each of said test ligands and the target protein under conditions appropriate for the target protein to unfold to an appropriate extent, thereby producing a test combination;
(c) incubating the target protein as in step (b), but in the absence of a test ligand, to produce a control combination;
(d) determining the extent to which the target protein occurs in a folded state, an unfolded state, or both, in the test combination and in the control combination;
(e) comparing the determination made in step (d) between the test and control combinations, wherein if the target protein is present in the folded state to a greater or lesser extent in the test combination than in the control combination, the test ligand is a ligand that binds to the target protein; and (f) repeating steps (b)–(e) with a plurality of said test ligands until at least one ligand that binds to the target protein is identified.

27. The method of claim 26, wherein in step (d), determining the extent to which target protein occurs in the folded state, the unfolded state, or both is carried out by a method selected from the group consisting of proteolysis, antibody binding, surface binding, molecular chaperone binding, differential binding to immobilized ligand and differential formation of aggregated protein.

28. The method of claim 27, wherein the determining step comprises the steps of:

(i) incubating the target protein, each of said test ligands, and one or more proteases that preferentially degrade target protein in its unfolded state, whereby the target protein in its unfolded state is degraded preferentially; and (ii) measuring the fraction of the target protein degraded or the fraction of the target protein remaining in an intact state, wherein if the fraction of targets protein remaining in the intact state in the test combination is greater or lesser than in the control combination, the test ligand is a ligand that binds to the target protein.

29. The method of claim 27, wherein the determining step comprises the steps of:

(i) combining the target protein and each of said test ligands;

(ii) exposing the target protein and the test ligand mixture to a surface which preferentially binds unfolded target protein, whereby unfolded target protein binds to the surface; and (iii) determining the fraction of the target protein bound to the surface or the fraction of the target protein remaining unbound, wherein if the fraction of target protein remaining unbound is greater or lesser in the test combination than in the control combination, the test ligand is a ligand that binds to the target protein.

30. The method of claim 27, wherein the determining step comprises the steps of:

(i) combining the target protein and each of said test ligands on a surface to which a known ligand of the target protein has been immobilized; and (ii) determining the fraction of the target protein bound to the surface or the fraction of the target protein remaining unbound wherein the fraction of target protein bound to the surface is greater or lesser in the test combination than in the control combination, the test ligand is a ligand that binds to the target protein.

31. The method of claim 27, wherein the determining step comprises using antibodies that distinguish between the folded form and the unfolded form of the target protein.

32. The method of claim 31, wherein the determining step further comprises the steps of:

(i) coating a surface with the target protein in its unfolded state or with peptide fragments of the target protein;

(ii) incubating an antibody directed against the unfolded state of the target protein in the presence of both the target protein and each of said test ligands; and (iii) determining the amount of the antibody bound to or remaining unbound to the surface.

33. The method of claim 31, wherein the determining step comprises the steps of:

(i) coating a surface with a specific antibody directed against the denatured state of the target protein;

(ii) incubating the target protein in the presence of each of said test ligands on the surface; and (iii) determining the fraction of the target protein bound to or not bound to the surface.

34. The method of claim 31, wherein the determining step comprises the steps of:

(i) coating a surface with an antibody capable of binding only the denatured state of the target protein;

(ii) incubating the target protein in the presence of each of said test ligands and an antibody directed against only the native state of the target protein; and (iii) determining the presence of the target protein bound or remaining unbound to the surface.

35. The method of claim 31, wherein the determining step comprises the steps of:

(i) coating a surface with an antibody capable of binding the native state of the target protein;

(ii) incubating the target protein in the presence of each of said test ligands and an antibody directed against the denatured state of the target protein; and (iii) determining the presence of the target protein bound or remaining unbound to the surface.

36. The method of claim 31, wherein the determining step comprises the steps of:

(i) coating a surface with an antibody capable of binding the denatured state of the target protein;

(ii) incubating the target protein in the presence of each of said test ligands and an antibody directed against only the folded state of the target protein; and (iii) determining the presence of the target protein bound or remaining unbound to the surface.

37. The method of claim 27, wherein the determining step comprises determining the amount of target protein bound to a molecular chaperone protein or not bound to a molecular chaperone protein.

38. The method of claim 37, wherein the determining step further comprises the steps of:

(i) coating a surface with a molecular chaperone protein;

(ii) incubating the target protein and each of said test ligands on the coated plate; and (iii) determining the amount of the target protein bound to or remaining unbound to the surface.

39. The method of claim 37, wherein the determining step comprises the steps of:

(i) coating a surface with the target protein in a denatured state;

(ii) incubating a purified form of the target protein in the presence of each of said test ligands and a molecular chaperone protein on the surface; and (iii) determining the amount of the molecular chaperone protein remaining unbound to or binding to the surface.

40. The method of claim 27, wherein the determining step comprises the steps of:

(i) coating a surface with antisera capable of binding to the folded target protein;

(ii) incubating the target protein in the presence of a molecular chaperone and each of said test ligands on the surface; and (iii) determining the amount of the target protein binding to or remaining unbound to the surface.

41. The method of claim 27, wherein the determining step comprises determining the differential formation of aggregated protein, using a method selected from the group consisting of:

(i) measuring the amount of aggregated protein; and (ii) measuring the amount of soluble protein and measuring the rate of formation of aggregated protein.

42. A method for high-throughput screening to identify a ligand that binds to human hemoglobin S, comprising the steps of:

(a) selecting as test ligands a plurality of compounds not known to bind to said hemoglobin;

(b) incubating each of said test ligands and said hemoglobin under conditions appropriate for said hemoglobin to unfold to an appropriate extent, thereby producing a test combination;

(c) incubating said hemoglobin as in step (b), but in the absence of a test ligand, to produce a control combination;

(d) determining the extent to which said hemoglobin occurs in a folded state, an unfolded state, or both, in the test combination and in the control combination;

(e) comparing the determination made in step (d) between the test and control combinations, wherein if said hemoglobin is present in the folded state to a greater or lesser extent in the test combination than in the control combination, the test ligand is a ligand that binds to the target protein; and (f) repeating steps (b)–(e) with a plurality of test ligands until at least one ligand that binds to said hemoglobin is identified.

43. The method of claim 42, wherein the determining step comprises the steps of:

(i) incubating the test and control combinations with one or more proteases that preferentially degrade said hemoglobin in its unfolded state, whereby said hemoglobin in its unfolded state is degraded preferentially;

(ii) measuring the fraction of said hemoglobin degraded or the fraction of said hemoglobin remaining in an intact state, wherein if the fraction remaining in the intact state in the test combination is greater than in the control combination, then the test ligand is a ligand that binds to said hemoglobin.

44. The method of claim 42, wherein said hemoglobin S comprises met-hemoglobin S.

45. The method of claim 43, wherein said one or more proteases are selected from the group consisting of proteinase K, trypsin, chymotrypsin, V8 protease, elastase, carboxypeptidase, proteinase K, thermolysin, papain and subtilisin.

46. A method for high-throughput screening to identify a ligand that binds to human hemoglobin S, comprising the steps of:

(a) selecting as test ligands a plurality of compounds not known to bind to said hemoglobin;

(b) incubating each of said test ligands and said hemoglobin under conditions appropriate for said hemoglobin to unfold to an appropriate extent, thereby producing a test combination;

(c) incubating said hemoglobin as in step (b), but in the absence of a test ligand, to produce a control combination;

(d) determining the extent to which said hemoglobin occurs in a folded state, an unfolded state, or both, in the test combination and in the control combination, wherein said determining step comprises incubating the test and control combinations with Proteinase K under conditions that preferentially degrade said hemoglobin in its unfolded state and measuring the fraction of said hemoglobin degraded or the fraction of said hemoglobin remaining in an intact state;

(e) comparing the determination made in step (d) between the test and control combinations, wherein if said hemoglobin is present in an intact state to a greater or lesser extent in the test combination than in the control combination, the test ligand is a ligand that binds to the target protein; and (f) repeating steps (b)–(e) with a plurality of test ligands until at least one ligand that binds to said hemoglobin is identified.

47. A method for high-throughput screening to identify a ligand that binds to human neutrophil elastase, comprising the steps of:

(a) selecting as test ligands a plurality of compounds not known to bind to said elastase;

(b) incubating each of said test ligands and said elastase under conditions appropriate for said elastase to unfold to an appropriate extent, thereby producing a test combination;

(c) incubating said elastase as in step (b), but in the absence of a test ligand, to produce a control combination;

(d) determining the extent to which said elastase occurs in a folded state, an unfolded state, or both, in the test combination and in the control combination, wherein said determining step comprises incubating the test and control combinations with Proteinase K under conditions that preferentially degrade said elastase in its unfolded state and measuring the fraction of said hemoglobin degraded or the fraction of said elastase remaining in an intact state;

(e) comparing the determination made in step (d) between the test and control combinations, wherein if said elastase is present in an intact state to a greater or lesser extent in the test combination than in the control combination, the test ligand is a ligand that binds to the target protein; and (f) repeating steps (b)–(e) with a plurality of test ligands until at least one ligand that binds to said elastase is identified.

* * * * *